US005222483A

United States Patent [19]

Plisek

[11] Patent Number: 5,222,483

[45] Date of Patent: Jun. 29, 1993

[54] ACOUSTIC PRESSURE PULSE GENERATOR

[75] Inventor: Franz Plisek, Erlangen, Fed. Rep. of Germany

[73] Assignee: Siemens Aktiengesellschaft, Munich, Fed. Rep. of Germany

[21] Appl. No.: 877,710

[22] Filed: May 4, 1992

[30] Foreign Application Priority Data

Jun. 5, 1991 [DE] Fed. Rep. of Germany ....... 4118443

[51] Int. Cl.[5] ........................ A61B 17/22

[52] U.S. Cl. ........................ 128/24 EL

[58] Field of Search ........................ 128/660.03, 24 EL; 606/127-128

[56] References Cited

U.S. PATENT DOCUMENTS

| | | | |
|---|---|---|---|
| 4,530,358 | 7/1985 | Forssman et al. | 128/24 EL |
| 4,669,472 | 6/1987 | Eisenmenger . | |
| 4,674,505 | 6/1987 | Pauli et al. . | |
| 4,697,588 | 10/1987 | Reichenberger . | |
| 4,715,376 | 12/1987 | Nowacki et al. | 367/147 X |
| 4,840,166 | 6/1989 | Naser et al. | 128/24 EL |
| 4,879,993 | 11/1989 | Reichenberger et al. | 128/24 EL |
| 4,928,672 | 5/1990 | Grasser et al. | 128/24 EL |
| 4,977,888 | 12/1990 | Rietter et al. . | |
| 5,031,626 | 7/1991 | Hassler et al. | 128/660.03 |
| 5,046,483 | 9/1991 | Ogura | 128/24 EL |
| 5,095,907 | 3/1992 | Kudo et al. | 128/24 EL X |

FOREIGN PATENT DOCUMENTS

| | | |
|---|---|---|
| 0131653 | 1/1985 | European Pat. Off. . |
| 0196353 | 10/1986 | European Pat. Off. . |
| 0242565 | 10/1987 | European Pat. Off. . |
| 3312014 | 10/1984 | Fed. Rep. of Germany . |
| 3525641 | 1/1987 | Fed. Rep. of Germany . |
| 3536073 | 4/1987 | Fed. Rep. of Germany . |
| 3605277 | 8/1987 | Fed. Rep. of Germany . |
| 8809252 | 12/1989 | Fed. Rep. of Germany . |
| 3835318 | 6/1990 | Fed. Rep. of Germany . |
| 9005596 | 8/1990 | Fed. Rep. of Germany . |
| 3926380 | 2/1991 | Fed. Rep. of Germany . |

*Primary Examiner*—Francis Jaworski
*Attorney, Agent, or Firm*—Hill, Steadman & Simpson

[57] ABSTRACT

An acoustic pressure pulse generator has a pressure pulse source in the form of a concussively driveable membrane, the membrane limiting a volume within the generator which contains a liquid acoustic propagation medium, the generator also having a wall therein spaced from the membrane, the wall dividing the volume into two sub-volumes. The acoustic propagation medium is circulated through an inlet in one of the sub-volumes and an outlet in the other sub-volume, with the two sub-volumes being in fluid communication via a flow restrictor through which the acoustic propagation medium flows. The restrictive effect of the flow restrictor is dimensioned so that the acoustic propagation medium contained in the sub-volume between the wall and the membrane is maintained at a pressure for effecting return of the membrane to its initial position after the membrane has been concussively driven.

9 Claims, 2 Drawing Sheets

ACOUSTIC PRESSURE PULSE GENERATOR

BACKGROUND OF THE INVENTION

1. Field of the Invention

The present invention is directed to a pressure pulse generator of the type having a pressure pulse source which creates acoustic pressure pulses in a liquid acoustic propagation medium by means of a concussively driveable membrane, also known as an electrodynamic pressure pulse generator.

2. Description of the Prior Art

Electrodynamic pressure pulse generators are used for a large variety of purposes. For example, such pressure pulse generators are used for medical purposes to non-invasively disintegrate calculi in the body of a patient, or to non-invasively treat pathological tissue conditions. For the first purpose, positive pressure pulses (greater than atmospheric pressure) are used, and in the latter application, negative pressure pulses (less than atmospheric pressure) are preferably used. Such pressure pulse generators, for example, may also be used in materials testing to charge material specimens with pressure pulses.

The pressure pulse generator is always acoustically coupled in a suitable manner to the subject to be acoustically irradiated, so that the pressure pulses generated in the acoustic propagation medium can be introduced into the subject with a minimum of reflections and energy loss. The pressure pulse generator and the subject to be acoustically irradiated must therefore be aligned relative to each other so that the region of the subject to be acoustically irradiated is located in the propagation path of the pressure pulses. If the pressure pulse generator is of the type which produces focused pressure pulses, it must also be assured that the region of the subject to be acoustically irradiated is located in the focal region of the focused pressure pulses.

A pressure pulse generator of this type is described in U.S. Pat. No. 4,674,505. This pressure pulse generator is a so-called electromagnetic shockwave generator which generates positive pressure pulses. This is accomplished by supplying high-voltage pulses to an electrically conductive coil arrangement, thereby causing the rapid build-up of a magnetic field. An electrically conductive membrane is disposed opposite the coil arrangement, and this magnetic field induces a current in the membrane in an opposite direction to the current flowing in the coil arrangement. The membrane current also is accompanied by a magnetic field, which is opposite in direction to the magnetic field associated with the coil arrangement. Repulsion forces are thereby rapidly produced, causing the membrane to be concussively moved rapidly away from the coil arrangement. The membrane interacts with an acoustic propagation medium to produce a pressure pulse therein, which gradually intensifies to form a shockwave along its propagation path.

A problem in pressure pulse generators of this type is that the membrane must be returned to its initial position after a pressure pulse has been generated. Only by doing so is it insured that the membrane will assume a defined position initial position before generating a further pressure pulse. It is important that the membrane assume such a defined initial position in order for successively generated shockwaves to coincide with sufficient precision with respect to their acoustic characteristics. A pressure pulse generator is disclosed by European Application 0 188 750, corresponding to U.S. Pat. No. 4,697,588 wherein return of the membrane to its initial position is accomplished by charging that side of the membrane facing away from the acoustic propagation medium with an under-pressure. Although the membrane is reliably returned to its initial position by this approach, a rather substantial design outlay is required and an under-pressure (suction) source must be provided.

A pressure pulse generator of the type described above is also disclosed in German OS 34 43 295, corresponding to U.S. Pat. No. 4,669,472, wherein the membrane is returned to its initial position by the acoustic propagation medium, which is maintained at a static pressure sufficient to accomplish this result. This approach has the disadvantage that the acoustic propagation medium adjacent the membrane cannot be conducted through a degasification means during operation of the pressure pulse generator, not can it be circulated through a cooling system in the manner disclosed by European Application 0 265 741, corresponding to U.S. Pat. No. 4,977,888. Degasification is desirable for removing gases dissolved in the acoustic propagation medium to prevent the formation of gas bubbles, which degrade the propagation of the pressure pulses. Cooling of the propagation medium is also desirable because a large amount of heat is dissipated during operation of the pressure pulse source, which must be eliminated in order to protect the pressure pulse source against premature failure due to elevated operating temperatures, primarily failure of the membrane which is subjected to high mechanical stresses.

SUMMARY OF THE INVENTION

It is an object of the present invention to provide a pressure pulse generator of the type having a concussively driven membrane having a simple and economical structure which permits cooling and degasification of the acoustic propagation medium while still maintaining the capability of generating successive pressure pulses having substantially coinciding acoustic characteristics.

The above object is achieved in accordance with the principles of the present invention in a pressure pulse source having a concussively driven membrane interacting with a liquid propagation medium wherein the membrane limits a volume containing the acoustic propagation medium, the generator having a rigid wall (i.e., a wall having sufficient mechanical strength so as to be pressure-resistant to the extent of not significantly transferring pressure on one side of the wall to the other side of the wall, at the pressures which are normally expected during the operation of the pressure pulse source) opposite and spaced from the membrane which subdivides the volume into two sub-volumes, with an inlet for circulating the acoustic propagation medium being disposed in one sub-volume and an outlet for the acoustic propagation medium being disposed in the other sub-volume. The sub-volumes are in fluid communication via a flow restrictor, through which the acoustic propagation medium flows, having a restrictive effect dimensioned so that the acoustic propagation medium contained in the sub-volume disposed between the wall and the membrane is maintained at a static pressure sufficient to effect return of the membrane to its initial position after it has been driven. The static pressure is higher than the ambient pressure.

Although the return of the membrane to its initial position in the pulse generator disclosed herein ensues by maintaining the acoustic propagation medium adjacent the membrane at an elevated pressure in comparison to the ambient pressure, the propagation medium is nonetheless circulated and, in preferred embodiments of the invention, can flow through a cooling unit and/or a degasification means. The pressure which prevails in the sub-volume between the membrane and the wall, which causes return of the membrane to its initial position, can be adapted to the particular requirements dependent on the flow (volume conveyed per time unit) of the acoustic propagation medium by selecting the restrictive effect of the flow restrictor, such as by varying the dimensions thereof, to achieve the desired pressure in the sub-volume situated between the between the membrane and the wall.

In a further embodiment of the invention, the restrictive effect of the flow restrictor can be variable, which can be achieved, for example, by the flow restrictor being in the form of an adjustable flow control valve.

Dependent on the stiffness of the membrane, an elevated pressure which is only slightly higher than the ambient pressure is sufficient for returning the membrane to its initial position, for example, the elevated pressure may be on the order of magnitude of less than 1 bar. Even if a large flow of the acoustic propagation medium is circulated, as is preferable, for cooling and degasification of the acoustic propagation medium, it is still possible to maintain the pressure in the sub-volume between the membrane and the wall at a level sufficient to return the membrane to its initial position. Preferably, the inlet for circulating the propagation medium discharges into the sub-volume disposed between the membrane and the wall, so that the acoustic propagation medium is maintained at the elevated pressure only at a location which is necessary to achieve the aforementioned desired effect.

A further embodiment of the flow restrictor may be at least one conduit having a stuitable cross section connecting the two sub-volumes in fluid communication. In practical embodiments of the invention, the wall is provided with at least one bore forming the flow restrictor, or alternatively at least one gap forming the flow restrictor can be present between the aforementioned wall and a neighboring component part.

In a preferred embodiment of the invention, the wall is shaped as an acoustic lens. This is particularly advantageous if the pressure pulses emanating from the membrane require focusing, and thus an acoustic lens will have to be provided in any event.

DESCRIPTION OF THE PREFERRED EMBODIMENTS

Figure 1:
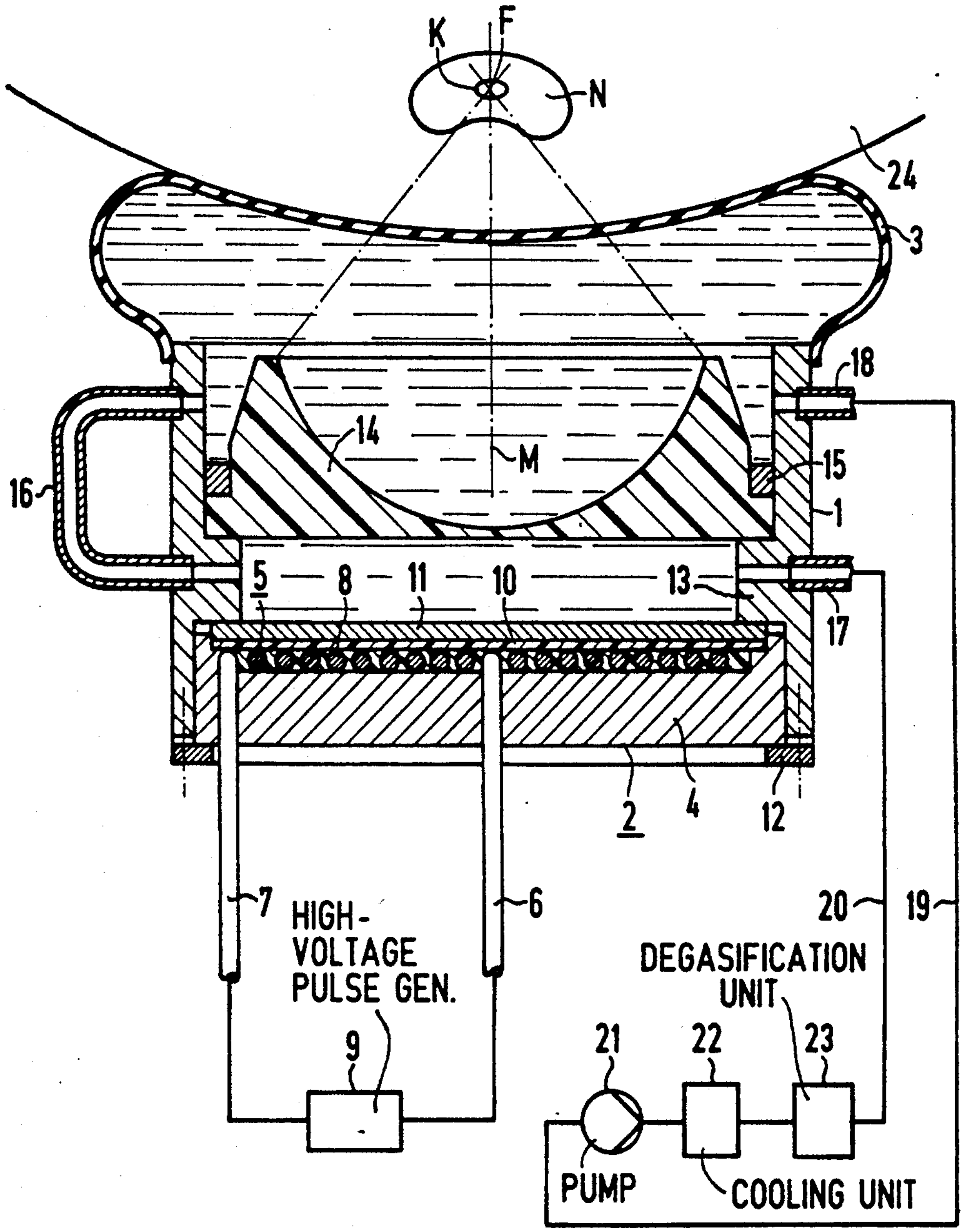
FIG. 1 is a longitudinal sectional view of a shockwave generator constructed in accordance with the principles of the present invention.

A pressure pulse generator constructed in accordance with the principles of the present invention is shown in FIG. 1 in the form of a shockwave generator for disintegrating calculi in the body of a patient. This shockwave generator has a tubular housing 1 with an end closed by an electromagnetic shockwave source, generally referenced 2, and an opposite end closed by a flexible coupling membrane 3. The shockwave source 2 has a coil arrangement in the form of a flat coil 5 arranged on a planar seating surface of a coil carrier 4. The flat coil 5 has terminals 6 and 7 connected by the spiral turns of the flat coil 5, one of these turns being referenced 8. The coil carrier 4 consists of electrically insulating material, for example aluminum oxide ceramic. The space between the turns of the coil 5 is filled with an electrically insulating casting resin. The terminals 6 and 7 are connected to a high-voltage pulse generator 9. The volume limited by the housing 1, the shockwave source 2 and the coupling membrane 3 is filled with a liquid acoustic propagation medium, for example water.

A circular disc-shaped, planar membrane 11 is disposed on that side of the flat coil 5 facing away from the coil carrier 4, with an insulating foil 10 disposed between the membrane 11 and the coil 5. The membrane 11 consists of electrically conductive material, for example copper. The membrane 11, the insulating foil 10 and the coil 5 are combined with the coil carrier 4 by means of a centering edge of the coil carrier 4 so as to form a unit. This unit is pressed against a shoulder 13, provided in the bore of the housing 1, by a ring 12 which presses against the coil carrier 4 and by a plurality of screws (only the center lines of two screws being shown with dashed lines).

The side of the membrane 11 facing away from the coil 5, which is adjacent to the acoustic propagation medium, is held against the shoulder 13 in liquid-tight fashion, possible with the use of suitable sealants (not shown).

A plano-concave acoustic lens 14 consisting of, for example, polystyrol, is disposed in the bore of the housing 1 opposite that side of the membrane 11 facing away from the coil 5, with its planar side facing toward the membrane 11. The positive lens 14 lies against that side of the shoulder 13 facing away from the membrane 11, and is axially fixed by a schematically-indicated retainer ring 15, and is pressed into the bore of the housing 1. The positive lens 14 thus subdivides the volume limited by the housing 1, the shockwave source 2 and the coupling membrane 3 into two sub-volumes. These sub-volumes are connected to each other by a flow restrictor in form of a pipe or hose line 16. Water is supplied to the shockwave generator through an inlet 17 which discharges into the sub-volume situated between the membrane 11 and the positive lens 14. Water flow is created through the line 16 into the sub-volume situated between the positive lens 14 and the coupling membrane 3 so that a volume of water corresponding to the water volume supplied through the inlet 17 is discharged through an outlet 18 leading from the latter sub-volume.

The outlet 18 and the inlet 17 via an outlet line 19 and an inlet line 20 between which a circulating pump 21, a cooling unit 22 and a degasification unit 23 are connected. The pressure which is present in the sub-volume between membrane 11 and positive lens 14 is dependent on the difference in pressure between the inlet 17 and the outlet 18, the magnitude of the water flow, and the restrictive effect of the line 16. As is known, the restrictive effect of the line 16 is substantially dependent on the length and the cross section of the line 16, and is also dependent on the nature of the surface of the interior wall of the line 16. Thus the aforementioned parameters can be easily selected so that not only is the elevated pressure required for returning the membrane 11 after generating a shockwave maintained in the sub-volume between the membrane 11 and the positive lens 14, but also a flow sufficient for proper cooling and degasification of the water is maintained.

Shockwaves are generated in a known manner with the shockwave generator described above, by charging the flat coil 5 with a high-voltage pulse from the high-voltage pulse generator 9. In response thereto, a magnetic field is generated by the flat coil 5 extremely quickly, which induces a current in the membrane 11 flowing in a direction opposite to the current flowing through the coil 5. The current in the membrane 11 is also accompanied by a magnetic field, this magnetic field being opposite in direction to the magnetic field associated with the coil 5. As a consequence of the repulsion forces generated by these oppositely directed fields, the membrane 11 is concussively moved rapidly away from the flat coil 5. As a result, a pressure pulse, which is initially planar, is introduced into the water contained in the sub-volume adjacent the membrane 11. This pressure pulse is focused onto a focal zone F by means of the positive lens 14 (as indicated with dot-dash lines in FIG. 1) onto a focal zone F which lies on the center axis M of the shockwave generator. The focused pressure pulse propagates in the water contained in the other sub-volume. Using the coupling membrane 3 with the assistance of a conventional locating system, for example an x-ray locating system, the shockwave generator is pressed against the body of a patient 24 to be treated, in such a position that the calculus K to be disintegrated, for example a stone in the kidney N, is located in the focal zone F. The calculus K can be disintegrated into fragments by means of a series of pressure pulses, the fragments being so small that they can be eliminated naturally. The pressure pulses emanating from the membrane 11 gradually intensify along their path through the propagation medium (water) situated in the two sub-volumes as well as through the body tissue of the patient 24 to form shockwaves, such shockwaves being pressure pulses with an extremely steep leading front.

As a consequence of the fact that the water contained in the sub-volume between the membrane 11 and the positive lens 14 is maintained at an elevated static pressure in comparison to the ambient pressure, it is assured after a pressure pulse has been generated that the membrane 11 will be returned to its initial position, wherein it lies flush against the surface of the flat coil 5, with the insulating foil 10 interposed therebetween. This insures that successively generated shockwaves will have the same acoustic characteristics. Moreover, since the acoustic propagation medium (water) is conveyed through the cooling unit 22 and through the degasification unit 23 by means of the circulating pump 21, it is assured that the water is cooled and degasified in the necessary manner. The cooling action of the cooling unit 22 is preferably such that the water supplied to the pressure pulse generator via the inlet 17 during normal operation has a temperature on the order of magnitude of the body temperature of the patient 24, so as to minimize discomfort to the patient. Moreover, as a consequence of the cooling and degasification of the water, a premature failure of the shockeave source 2, particularly a failure of the membrane 11, due to excessively high operating temperatures and disturbances in the propagation of the generated shockwaves by gas bubbles, is avoided.

Figure 2:
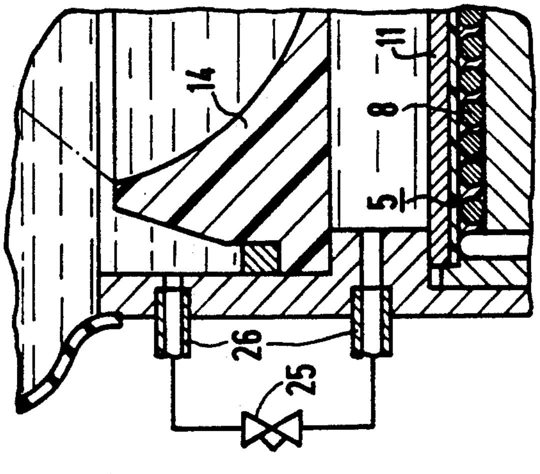

One version for the flow restrictor constructed in accordance with the principles of the present invention is shown in FIG. 2. The flow restrictor in this embodiment is formed by a flow control valve 25 disposed in a line 26 which connects the two sub-volumes of the shockwave generator in fluid communication. The cross section of the line 26 is preferably (but not necessarily) dimensioned so that the flow restricting effect of the line 26 is negligible in comparison to that of the flow control valve 25. As shown, the restrictive effect of the flow control valve 25 is adjustable, so that the elevated pressure present in the sub-volume between the membrane 11 and the positive lens 14 is variable.

Figure 3:
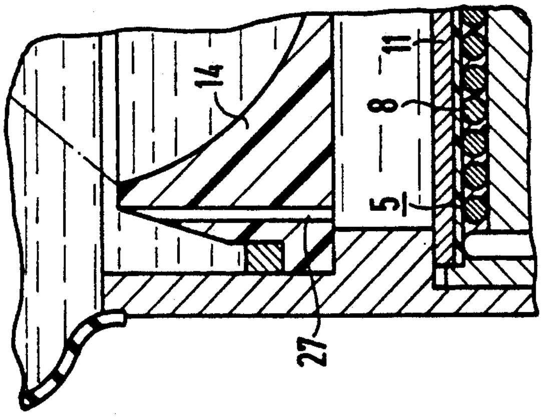

Another embodiment of a flow restrictor is shown in FIG. 3. In this embodiment, the flow restrictor is formed by a bore 27 in the positive lens 14, connecting the two sub-volumes in fluid communication. The bore 27 is dimensioned in terms of its length, diameter, etc., so that the necessary flow restriction for creating an elevated pressure which returns the membrane 11 to its initial position is achieved. It is also possible to provide a plurality of bores 27, with the combined, total restrictive effect of these bores being similarly dimensioned to achieve the necessary elevated pressure for returning the membrane 11 to its initial position.

Figure 4:
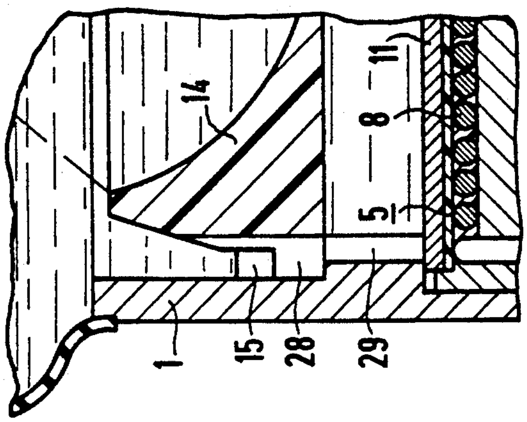
FIGS. 2, 3 and 4 are enlarged sectional views of a portion of the apparatus of FIG. 1, respectively showing different embodiments of a flow restrictor constructed in accordance with the principles of the present invention.

In the embodiment of FIG. 4, the flow restrictor is formed by a gap between the outer edge of the positive lens 14 and the interior surface of the housing 1. The positive lens 14 has an outer surface provided with a continuous, substantially axially proceeding channel 28, which discharges into a continuous slot 29 of the shoulder 13, the slot 29 also proceeding substantially axially. The restrictive effect of this gap is essentially dependent on the geometry thereof, which is selected to achieve the necessary elevated pressure for returning the membrane 11 to its initial position. The retainer ring 15 also has a slot disposed in the region of this gap.

Some pressure pulse generators do not require a positive lens. Such generators may be used to generate unfocused pressure pulses for applications wherein focused pressure pulses are not needed. In other types of pressure pulse generators having no positive lens, the membrane is shaped in such a manner, for example spherically curved, so that the pressure pulses emanating from the membrane are already focused. In such pressure pulse generators which do not have a positive lens, a flat wall having opposite end faces in parallel planes is provided instead of the positive lens 14 shown in the embodiments of FIGS. 1 through 4.

Although the invention has been described herein in the context of the example of a shockwave generator for medical purposes, the inventive concept disclosed herein can also be employed in other pressure pulse generators. Moreover, the inventive concept disclosed herein can be employed in pressure pulse generators wherein the membrane is driven in some manner other than electromagnetically.

Although further modifications and changes may be suggested by those skilled in the art, it is the intention of the inventor to embody within the patent warranted hereon all changes and modifications as reasonably and properly come within the scope of his contribution to the art.

I claim as my invention:

1. A pressure pulse generator comprising:

a housing having a volume containing an acoustic propagation medium;

a pressure pulse source in said housing including a membrane limiting said volume and means for concussively driving said membrane for causing said membrane to interact with said acoustic propagation medium to generate an acoustic pressure pulse therein;

rigid divider means separating said volume into first and second sub-volume;

an inlet in fluid communication with one of said sub-volumes and an outlet in fluid communication with the other of said sub-volumes and means for circulating said acoustic propagation medium through said inlet and said outlet; and flow restrictor means placing said sub-volumes in fluid comminication for restricting flow of said acoustic propagation medium from one sub-volume to the other for maintaining a static pressure in the sub-volume disposed between said divider means and said membrane for effecting return of said membrane to an initial position after said membrane has been concussively driven.

2. A pressure pulse generator as claimed in claim 1 further comprising means for cooling said acoustic propagation medium as said acoustic propagation medium flows from said outlet to said inlet.

3. A pressure pulse generator as claimed in claim 1 further comprising means for degasifying said acoustic propagation medium as said acoustic propagation medium flows from said outlet to said inlet.

4. A pressure pulse generator as claimed in claim 1 further comprising means for varying the restrictive effect of said flow restrictor.

5. A pressure pulse generator as claimed in claim 1 wherein said inlet is disposed for discharging said acoustic propagation medium into said sub-volume disposed between said divider means and said membrane.

6. A pressure pulse generator as claimed in claim 1 wherein said flow restrictor means is formed by at least one hole in said divider means.

7. A pressure pulse generator as claimed in claim 1 wherein said flow restrictor is formed by a gap between said divider means and a neighboring part.

8. A pressure pulse generator as claimed in claim 1 wherein said divider means is shaped as an acoustic lens.

9. A pressure pulse generator as claimed in claim 1 wherein said membrane consists of electrically conductive material and wherein said pressure pulse source includes an electrical coil disposed opposite a side of said membrane facing away from said acoustic propagation medium, and means electrically connected to said coil for driving said membrane.

* * * * *